United States Patent [19]
Frischauf

[11] Patent Number: 5,371,020
[45] Date of Patent: Dec. 6, 1994

[54] METHOD OF PHOTOMETRIC IN VITRO DETERMINATION OF THE CONTENT OF AN ANALYTE IN A SAMPLE

[75] Inventor: Peter A. Frischauf, Broendby, Denmark

[73] Assignee: Radiometer A/S, Copenhagen, Denmark

[21] Appl. No.: 50,100

[22] PCT Filed: Sep. 17, 1991

[86] PCT No.: PCT/DK92/00280
§ 371 Date: May 7, 1993
§ 102(e) Date: May 7, 1993

[87] PCT Pub. No.: WO93/06456
PCT Pub. Date: Apr. 1, 1993

[30] Foreign Application Priority Data
Sep. 19, 1991 [DK] Denmark .............. 1613/91

[51] Int. Cl.$^5$ ............................................. G01N 21/03
[52] U.S. Cl. ................................. 436/165; 436/68;
436/164; 422/82.05; 422/82.09; 356/39;
356/246; 356/320; 356/434; 356/440
[58] Field of Search ............... 436/68, 164, 165, 171;
422/58, 82.05, 82.06, 82.09, 82.11; 356/39, 40,
246, 434, 320, 440

[56] References Cited

U.S. PATENT DOCUMENTS

| | | | |
|---|---|---|---|
| 3,740,156 | 6/1973 | Heigl et al. | 356/246 X |
| 3,810,695 | 5/1974 | Shea | 356/246 X |
| 4,509,522 | 4/1985 | Manuccia et al. | 128/634 |
| 4,762,798 | 8/1988 | Deutsch | 436/165 X |
| 4,786,171 | 11/1988 | LeFebre et al. | 356/440 X |
| 4,873,993 | 10/1989 | Meserol et al. | 356/39 X |
| 4,980,551 | 12/1990 | Wong | 356/440 X |
| 4,997,769 | 3/1991 | Lundsguard | 422/82.09 X |
| 5,099,123 | 3/1992 | Harjunmaa | 356/39 X |
| 5,139,333 | 8/1992 | Reinhard | 356/440 X |
| 5,149,503 | 9/1992 | Kohno et al. | 422/82.05 |
| 5,168,367 | 12/1992 | O'Rourke et al. | 356/246 |

FOREIGN PATENT DOCUMENTS

| | | |
|---|---|---|
| 0253559A1 | 1/1988 | European Pat. Off. . |
| 2160646A | 5/1984 | United Kingdom . |
| WO90/07106 | 6/1990 | WIPO . |
| WO90/07109 | 6/1990 | WIPO . |

OTHER PUBLICATIONS

Skoog, D. A. West, D. M., "Fundamentals of Analytical Chemistry," 4th ed., pp. 501-524 Philadelphia: Saunders College Publishing, 1982.

Hummel, D. O., "Atlas der Kunststoff-Analyse," Ban 1, Teil 1., Müchen: Carl Hauser Verlag, 1968 (with English Abstract).

PCT International Search Report for PCT Application No. PCT/DK92/00280 corresponding to the present application.

Primary Examiner—James C. Housel
Assistant Examiner—Maureen M. Wallenhorst
Attorney, Agent, or Firm—David M. Klein

[57] ABSTRACT

A method of photometric in vitro determination of the content of an analyte in a sample is disclosed. The sample is located in a measuring chamber which has a radiation path length and has at least one at least partially transparent wall part. The measuring chamber is in optical communication with an optical system adapted for the analyte which includes a radiation source and a radiation detector. The measuring chamber is adjustable in shape which enables the radiation path length across the measuring chamber to be changed. In a first measuring step an unknown first radiation path length across the measuring chamber is set and radiation at at least two wavelengths is transmitted from the radiation source through the measuring chamber and to the radiation detector. In a second step, the measuring chamber is adjusted in shape thereby setting a second unknown path length across the measuring chamber. Radiation at the same wavelengths as during the first step is again transmitted from the radiation source through the measuring chamber and to the radiation detector. The analyte content is then determined on the basis of radiation detected in each of the measuring steps.

27 Claims, 8 Drawing Sheets

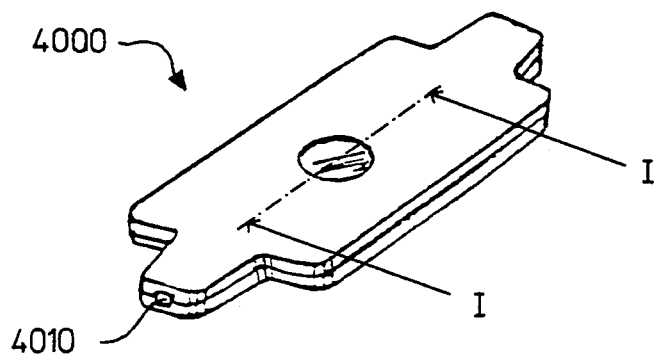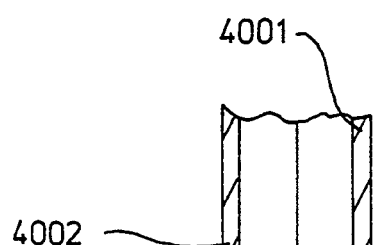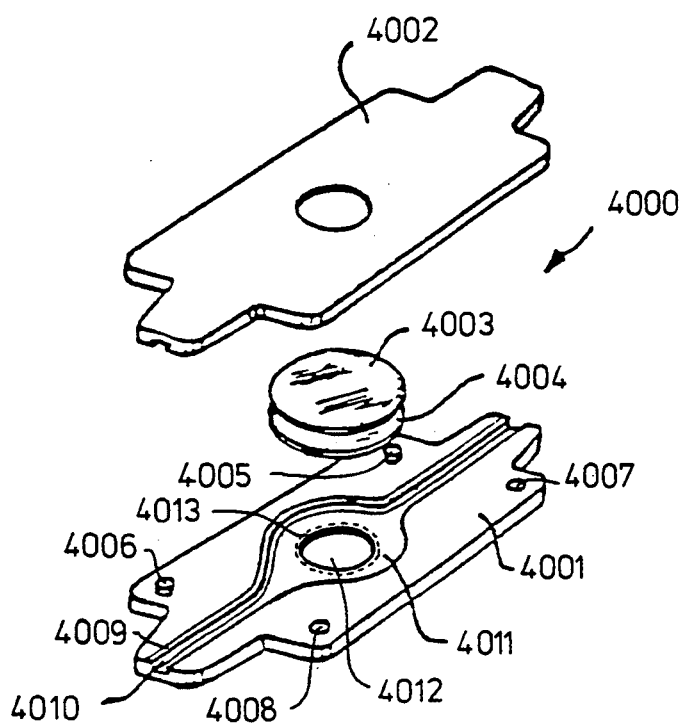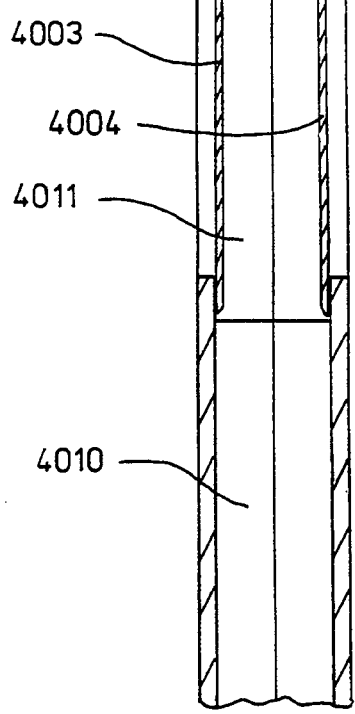
FIG. 1a
FIG. 1b
FIG. 1c

5,371,020

METHOD OF PHOTOMETRIC IN VITRO DETERMINATION OF THE CONTENT OF AN ANALYTE IN A SAMPLE

BACKGROUND OF THE INVENTION

1. Field of the Invention

The present invention relates to a method of photometric in vitro determination of the content of an analyte in a sample located in a measuring chamber device with a measuring chamber which has a defined radiation path length and has one at least partially transparent wall part, said measuring chamber being in optical communication with an optical system adapted for the analyte and comprising a radiation source and a radiation detector.

2. Description of the Related Art

In photometric analysis of the analyte content in a sample located in a measuring chamber, it is in certain cases desired, for example in connection with blood measurements, to make the measuring chamber wall parts located in the radiation transmission path very thin. This may for example be required if the wall parts of a measuring chamber are made from a material significantly absorbing the measuring radiation. In certain instances the thin wall parts may, however, give rise to errors in the determination of the analyte content. E.g. this situation will arise when the radiation wavelength is comparable to the optical thickness of the measuring chamber walls, said optical thickness being defined as the physical thickness of the walls multiplied by the refraction coefficient of the wall material. Thus, the problem is mainly connected with long wave measuring radiation such as infrared or near-infrared radiation.

When the measuring chamber wall has smooth, plano-parallel surfaces, radiation will be reflected and/or refracted in the interfaces between the surroundings and the external walls of the measuring chamber and in the interfaces between the internal walls of the measuring chamber and the sample, respectively. The extent to which the radiation is reflected and/or refracted depends on the refraction coefficients for the wall material, the surroundings and the sample. Said reflected and/or refracted radiation gives rise to a sinusoidal interference spectrum which superposes the measuring spectrum. Particularly in cases where absorption caused by the analyte is relatively small, the above interference spectrum may dominate the measuring spectrum.

The interference spectrum is extremely dependent on the thickness of the walls, and even small variation in thickness will displace the spectrum considerably. Such small variation is almost impossible to avoid in automated mass-production without extremely great expense. Therefore, each measuring chamber device will have its own characteristic interference spectrum.

The effect of interference in connection with foils is disclosed in Hummel/Schou, "Atlas der Kunststoff-Analyse", 1968, ps. 64–65. In this reference a possible solution to the problem is also given; namely to provide one of the parallel sides with a fine roughness in order that the reflected radiation beams do not interfere, but are being scattered diffusely. However, this method is not very advantageous when a large number of uniform products are to be produced as the roughness must be very fine in order to remove interference completely. The roughening of the foil will result in an additional expensive manufacturing process step and further it is difficult to ensure that all products be provided with the same roughness and thereby with the same radiation transmission properties.

SUMMARY OF THE INVENTION

The object of the invention is to provide a method by which the problems mentioned in respect of photometric analysis of a sample located in a measuring chamber are eliminated.

This is achieved by the method according to the invention, said method being characterized in using a measuring chamber which is adjustable in shape, the adjustment in shape controlling the setting of the radiation path length across the measuring chamber, setting in a first measuring step a first radiation path length across the measuring chamber, transmitting radiation at at least one wavelength from the radiation source through the measuring chamber and to the radiation detector, subsequently setting in a second measuring step a second radiation path length across the measuring chamber by adjusting the shape of the measuring chamber, transmitting radiation at the same wavelength as during the first measuring step from the radiation source through the measuring chamber and to the radiation detector, and determining the analyte content on the basis of radiation detected in each of the measuring steps.

In the present context, the term "photometric determination" includes any determination based on measuring of changes in electromagnetic radiation, which under controlled conditions is emitted, transmitted, absorbed or reflected. A general description of photometric determination and optical analyzers is disclosed in "Fundamentals of Analytical Chemistry", Skoog, D.A. & West, D.M., chapter 20, ps. 501–524.

Setting the first radiation path length may consist in letting the radiation path length across the measuring chamber equal the initial path length, i.e. the path length of the measuring chamber in its original unadjusted shape or in establishing another path length by adjusting the shape of the measuring chamber.

One of the two radiation path lengths may be set to zero so that all of the sample is drained from the radiation transmission path in the measuring chamber. Radiation detected at this radiation path length represents absorption and interference from the optical system and the measuring chamber only. Measuring the sample is performed at the other radiation path length, which must not be zero.

Radiation transmitted from the radiation source may be wide-band radiation as well as monochromatic radiation and may belong to the ultraviolet range, the visible range, the near-infrared range and/or the infrared range. The radiation source may comprise one single component or several components transmitting radiation at their respective particular wavelength ranges.

The radiation detector may also comprise one single component detecting radiation in a particular wavelength range or several components detecting radiation in their respective particular wavelength ranges. In case that the radiation source comprises several components, said components may be integrated in a unit or comprise several physically separated units. The same applies to the radiation detector.

The method according to the invention is, as mentioned above, particularly advantageous when the wavelength of the measuring radiation is comparable to the optical thickness of one or more wall parts in the measuring chamber. It has been found that a ratio between the optical thickness and the measuring wavelength above approx. 50 usually lies beyond the range in which unacceptable interference takes place.

The measuring chamber device may be provided in several embodiments. One embodiment may comprise a measuring chamber block provided as a fixed component of an analyzer, said measuring block having a measuring chamber for measuring consecutively on a large number of samples. Another embodiment may comprise a single-use device insertable in an optical analyzer adapted for the particular measuring chamber device.

An analysis system with a single-use device of the type mentioned above is for example disclosed in Applicant's International Patent Application WO 90/07106. This application discloses a method and a system for photometric in vitro determination of a blood gas parameter in a blood sample. The blood sample is transferred directly from a patient to a measuring chamber in a sample container, which subsequently is brought into optical communication with an optical system. Measurement of the blood gas parameter, i.e. $CO_2$ is performed by transmitting radiation through the sample located in the measuring chamber having a fixed radiation path length.

Applicant's International Patent Application WO 90/07109 discloses a method and an analyzer for photometric in vitro determination of the content of an analyte in a sample of whole blood. The sample is transferred from the patient directly to a measuring chamber comprising a transparent body, the radiation transmission characteristics of said transparent body depending on the concentration of the particular analyte in the sample. After filling the measuring chamber, the transparent body is equilibrated with the sample whereafter the measuring chamber is deformed in a controlled manner draining the part of the measuring chamber located in the radiation transmission path for sample. The analyte content is then determined on the basis of detection of radiation transmitted through the measuring chamber and the transparent body. None of the measurements are performed directly on the sample in this system due to the fact that the sample has been drained from the radiation transmission path before a measurement is performed.

In a preferred embodiment of the present invention a measuring chamber is used wherein the optical transmission properties of the wall parts located in the radiation transmission path are essentially independent of the adjustment of the measuring chamber.

Due to the fact that the measuring chamber wall parts located in the radiation transmission path do not change their optical transmission characteristics when the shape of the measuring chamber is adjusted, the interference spectrum produced at the surfaces of the wall parts is similar at the two radiation path lengths across the measuring chamber. Thus, by comparing the measurement results from the two different radiation path lengths, the contribution from the interference spectrum may be removed completely in the determination of the analyte content.

In another preferred embodiment of the invention a measuring chamber is used comprising two opposite at least partially transparent wall parts located in the radiation transmission path.

In a further embodiment of the invention a measuring chamber is used comprising one at least partially transparent wall part and one opposite wall part reflecting incoming radiation, said wall parts being located in the radiation transmission path as well.

In a preferred embodiment the adjustment in shape of the measuring chamber is provided by displacement of at least one of the measuring chamber wall parts located in the radiation transmission path.

The content of a particular analyte in a sample is calculated on the basis of measurements of the transmission properties of the sample at at least one wavelength, which must fall within a range where the particular analyte absorbs.

In photometric determination of an analyte in a sample, in which the solvent is strongly absorbing at the measuring wavelength, it is usually attempted to make the radiation path length through the sample very short in order to reduce loss of energy, generation of heat in the sample, etc. The setting of a short radiation path length makes, however, heavy demands on the mechanical accuracy of the analyzer and even minor inaccuracies in the radiation path length may have a decisive influence on the measuring result. The problem may be overcome by determining the radiation path length in each measurement.

In a preferred embodiment of the invention radiation at a wavelength additional to the at least one wavelength is transmitted from the radiation source through the measuring chamber and to the radiation detector and the difference between the first and second radiation path lengths is determined on the basis of the radiation detected at each of the wavelengths in each of the measuring steps. The difference between the first and second radiation path lengths equals the effective radiation path length through the sample as described more closely in the detailed part of the specification.

In an embodiment of the method according to the invention the content of one additional analyte in the sample may be determined simultaneously with the first analyte by including radiation at one additional wavelength in the measuring steps. This additional wavelength must be a wavelength where said one additional analyte absorbs. Correspondingly, a number of additional analytes may be determined by including a number of additional wavelengths at least equal to the number of additional analytes.

The method according to the invention is especially useful in connection with analytes which at the measuring wavelength absorb weakly compared to the solvent, the analyzer and/or the measuring chamber. In this case the measuring spectrum relating to the analyte will to a considerable degree be superposed by the interference spectrum of these other constituents or parts.

In a preferred embodiment of the invention the $CO_2$ content in a sample is determined on the basis of an examination of the transmission characteristics of the sample for radiation at wavelengths at approx. 4228 nm, 4268 nm and 4308 nm. Determination of the $CO_2$ content by irradiating with radiation at said wavelengths is disclosed in i.a. Applicant's above-mentioned International Patent Application WO 90/07106. In the specification of U.S. Pat. No. 4509522, Manuccia et al. a photometric method for in vivo determination of the content of blood gases in blood is disclosed; i.a. $CO_2$ is determined by irradiating with radiation at approx. 4.2 $\mu$m. The basic principles for determining $CO_2$ by transmission measurement at a wavelength of approx. 4.2 $\mu$m is disclosed in the specification of British Patent Application GB 2160646, Mosse, C. A. & Hillson, P. J. and in the specification of European Patent Application EP 253559, Nestor, J. R. The content of said publications is considered incorporated into the present application by reference to the publications.

The invention further relates to an analyzer for use in the method according to the invention, said analyzer comprising a radiation source, a radiation detector and a measuring chamber device with a measuring chamber, said measuring chamber having at least one at least partially transparent wall part and being in optical communication with the radiation source and the radiation detector, and being characterized in that the measuring chamber is adjustable in shape, that the analyzer is provided with means which are adapted to adjust the measuring chamber in shape in a controlled manner and which when activated set first and second radiation path lengths, respectively, across the measuring chamber, and that the radiation source is adapted to transmit radiation at at least one wavelength through the measuring chamber to the radiation detector at the respective first and second radiation path lengths.

Preferably, the analyzer according to the invention comprises means for converting the radiation detected and means for processing the converted radiation data in order to derive the content of the analyte in the sample. Alternatively, the data processing means may be comprised in a separate data processing unit connectable to the analyzer.

Further it is preferred that the analyzer comprises means for displaying the analyte content. Alternatively, the analyzer is adapted for connection to display means, such as for example a data screen, a display, a printer or a plotter.

The invention further relates to a measuring chamber device with a measuring chamber for use in an analyzer according to the invention, said measuring chamber device being characterized in that the measuring chamber is adjustable in shape in a controlled manner setting first and second radiation path lengths across the measuring chamber.

In a preferred embodiment of the measuring chamber device the optical transmission characteristics of the measuring chamber wall parts adapted to be placed in the radiation transmission path are essentially independent of the adjustment in shape of the measuring chamber.

Preferably, the measuring chamber comprises two opposite at least partially transparent wall parts, but it may comprise one at least partially transparent wall part and one opposite wall part reflecting incoming radiation.

The measuring chamber device may include one single measuring chamber or several measuring chambers arranged in series or in parallel. Preferably, the measuring chamber device is made from an injection mouldable polymeric base material. A suitable base material is polyethylene terephthalate (PETP), which for example is sold under the tradename ARNITE$^m$ from AKZO, Arnhem, Holland.

The partially transparent wall parts and the measuring chamber device proper may differ in material. The wall material is primarily selected on the basis of its transmission properties at the measuring wavelengths and its applicability in the manufacturing process of the entire measuring chamber device.

When using a measuring chamber device in the form of a single-use component, the optical communication between the radiation source, the radiation detector, and the measuring chamber device may be established by placing the measuring chamber device in a particular station in the analyzer. Alternatively, the optical communication may be established by means of one or several optical fiber cables connecting contact elements on the measuring chamber device to the analyzer.

BRIEF DESCRIPTION OF THE DRAWINGS

The invention will now be further explained in the following with reference to the drawing and the subsequent examples. In the drawing:

FIGS. 1a and b show perspective views of a measuring chamber device for use in the method according to the invention;

FIG. 1c shows a sectional view on an enlarged scale along the line I—I in FIG. 1a;

In the different figures same parts are provided with identical reference numerals.

DESCRIPTION OF THE PREFERRED EMBODIMENT

FIGS. 1a and b show an embodiment of a measuring chamber device for use in determination of an analyte in a sample. The measuring chamber device, generally designated 4000, is part of an analyzer having an optical unit as further described below in connection with FIG. 4. The measuring chamber device 4000 consists of two identical halves 4001 and 4002. Said halves are made by means of injection moulding of a transparent "soft" plastic material, for example polyethylene terephthalate (PETP) of the type ARNITE TM from AKZO, Arnhem, Holland. The two halves are assembled by pins 4005 and 4006 in the half 4001 engaging mating, not shown recesses in the half 4002, while not shown pins in the latter engage recesses 4007 and 4008 in the half 4001. Thereafter, the two halves are welded together by means of ultrasonic welding.

The line of material 4009 outlined in the half 4001 shown in the figure as the lower half forms a welding seam after the welding. Said line of material lies along the edge of a longitudinal open conduit 4010, which centrally expands transversely and forms a measuring chamber 4011 with a through hole 4012 directed perpendicular to the conduit 4010. The through hole 4012 is covered by a window 4004 made from a 23 μm foil of polyethylene terephthalate (PETP) of the type Melinex S from ICI, Cheshire, England. The corresponding through hole in the half 4002 is covered by a similar window 4003.

The windows 4003 and 4004 are mounted in the halves 4001 and 4002 prior to assembly. The mounting of the window 4004 is carried out by said 23 μm PETP foil being stretched across the through hole 4012 in the half 4001 whereafter the foil by means of an ultrasonic welding head is welded to the half 4001 in a border area 4013 next to the through hole 4012. The excessive foil is then punched by means of a perforating punch leaving only the fixedly welded window 4004. By stretching the foil across the hole 4012 it is ensured that the window 4004 is plane after the ultrasonic welding. The window 4003 is affixed to the cuvette half 4002 in a similar manner. The windows 4003 and 4004 are elastically displaceable in a direction perpendicular to the conduit 4010.

FIG. 1c, which is a view along the line I—I of FIG. 1a, shows the central part of the measuring chamber device 4000 with the measuring chamber 4011 delimited by the windows 4003 and 4004.

Figure 2:
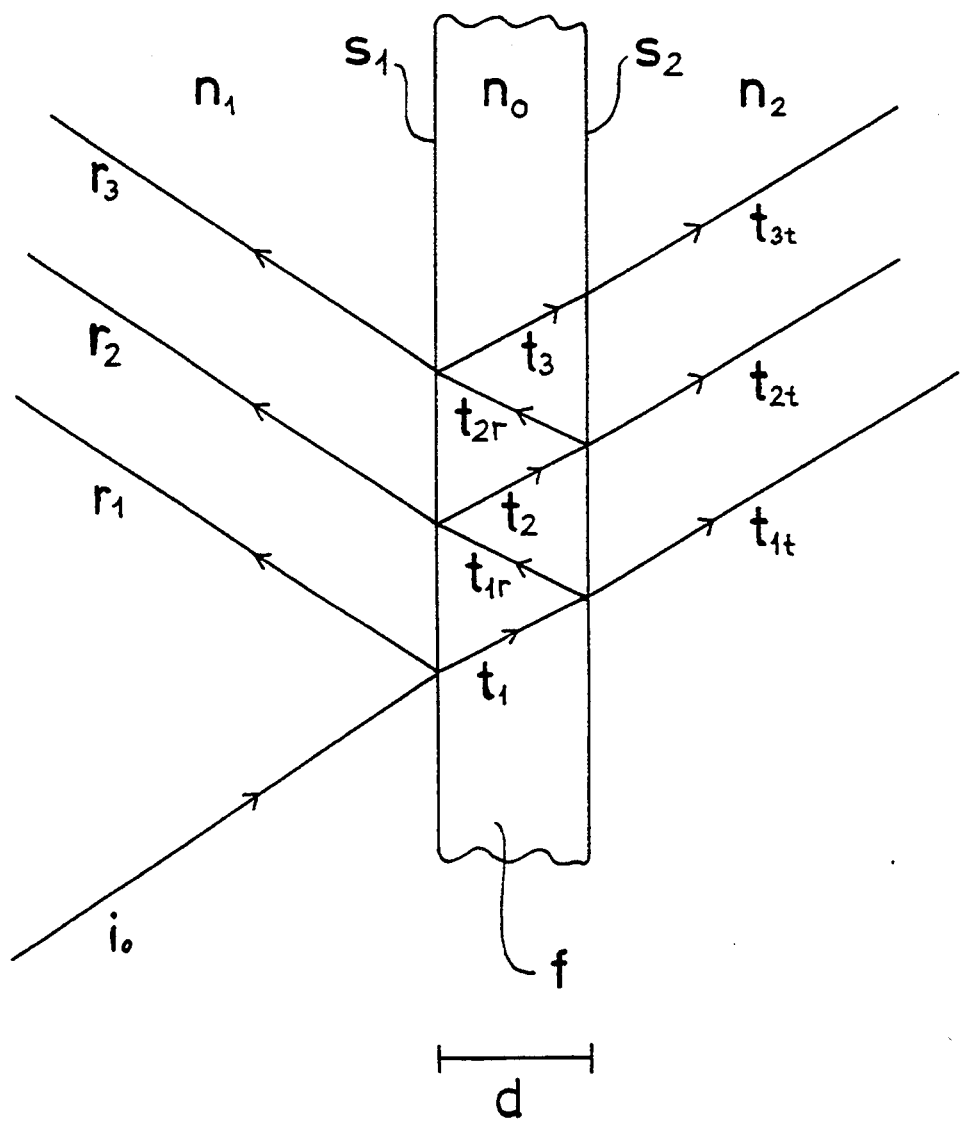
FIG. 2 shows interference obtained by transmitting radiation towards a thin foil with two plano-parallel surfaces.

In FIG. 2 is shown a section of a foil f with a refraction coefficient $n_o$ and provided with plano-parallel, smooth surfaces $s_1$ and $s_2$. A radiation beam $i_o$ with a particular measuring wavelength is transmitted towards the surface $s_1$. Assuming that the incoming radiation $i_o$ has an angle of incidence less than the critical angle for total reflection, the incoming radiation will, when falling onto the external, smooth surface $s_1$ of the foil f, split into a reflected beam $r_1$ and a transmitted beam $t_1$ depending on the refraction coefficients $n_1$ and $n_2$ of the adjacent materials. The transmitted beam $t_1$ will, when falling onto the internal, smooth foil surface $s_2$, split into a transmitted $t_{1t}$ and a reflected $t_{1r}$ beam, which again will split into a reflected $t_2$ and a transmitted $r_2$ beam.

When the optical thickness of the foil f is comparable to the wavelength $i_o$ of the incoming radiation, the reflected beams $r_1, r_2, r_3 \ldots$ will interfere constructively or destructively dependent on the phase differences. This applies to the transmitted beams too. The interference gives rise to a sinusoidal interference spectrum, which influence the transmission spectrum of the foil. The following relation applies between the thickness d of the foil and the interference spectrum obtained at the plano-parallel surfaces $s_1, s_2$:

$$d = \frac{1}{2n_o} \left( \frac{1}{\lambda_a} - \frac{1}{\lambda_b} \right)^{-1} \quad (1)$$

where d is the thickness of the foil;
$n_o$ is the refraction coefficient of the foil;
$\lambda_a, \lambda_b$ are wavelengths in the interference spectrum; and
$\lambda_b-\lambda_a$ is a wavelength interval corresponding to one period in the interference spectrum.

As seen from (1), a change in the thickness of the foil d will cause a displacement of $\lambda_a$ in relation to $\lambda_b$ and consequently a change of the period of the interference spectrum. As it is impossible in practice to make the foil windows 4003 and 4004 in a series of measuring chamber devices 4000 completely identical in thickness each measuring chamber device will have a characteristic interference spectrum from the foil windows. This means that the analyzer cannot be set in advance to compensate for the interference spectrum.

Figure 3:
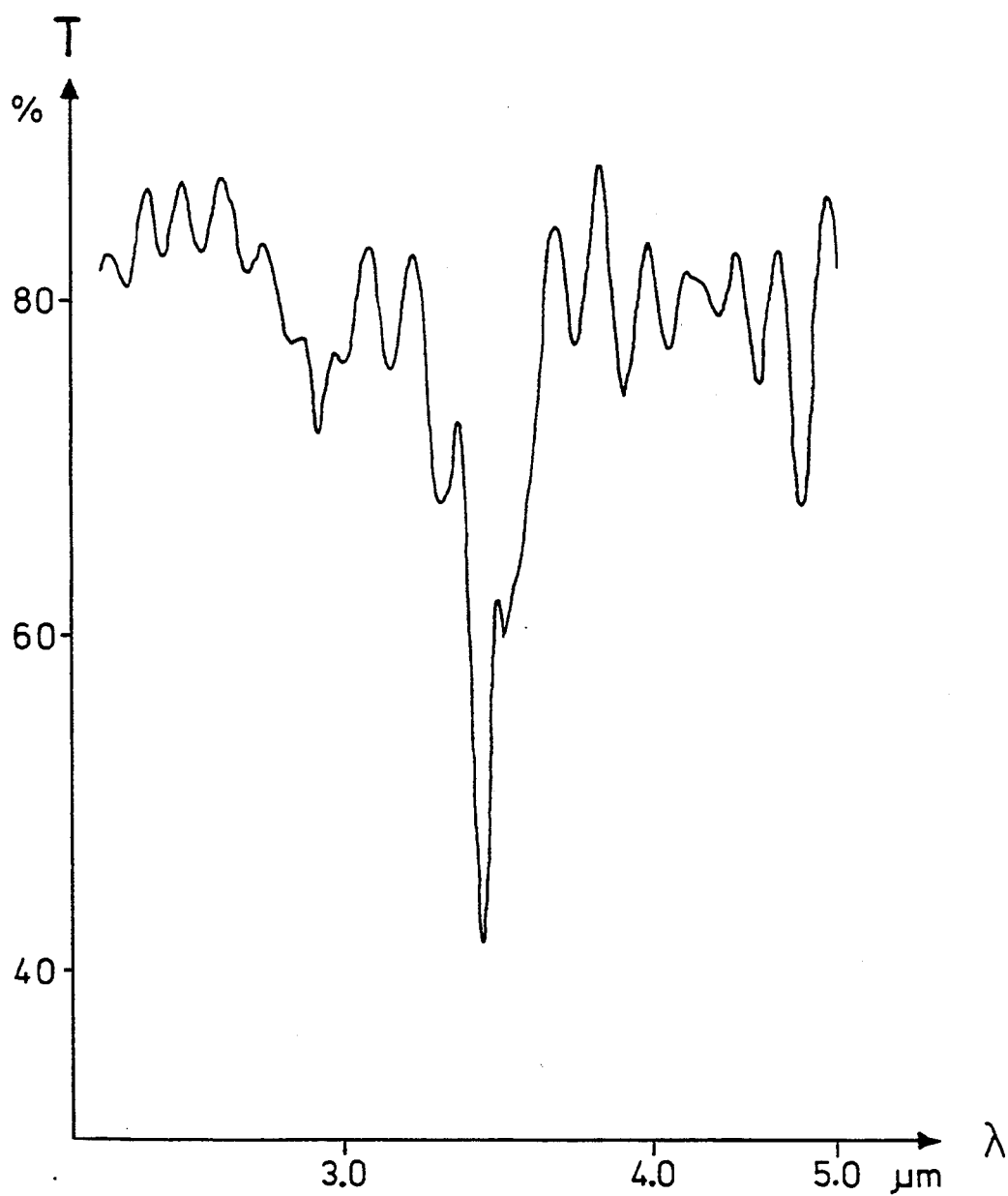
FIG. 3 shows an absorption spectrum for a 23 μm foil of polyethylene terephthalate (PETP)

FIG. 3 shows an absorption spectrum in the wavelength range 2500–5000 nm for a 23 μm foil of PETP corresponding to the foil used for the windows 4003 and 4004 in the measuring chamber 4011 of the measuring chamber device. The spectrum is recorded on a spectrophotometer of the type 157 from PERKIN-ELMER. As seen from the figure, the foil is relatively transparent to radiation in the range mentioned, as approx. 80% of the transmitted radiation is transmitted through the foil when the special absorption bands relating to the material PETP are disregarded (for example at a wavelength of approx. 3380 nm). Moreover, it is seen from FIG. 3 that the spectrum for the material is superposed by an apparently sinusoidal interference spectrum. The superposed spectrum results from interference of radiation refracted/reflected on the smooth surfaces of the foil, cf. the above description of FIG. 2.

Figure 4:
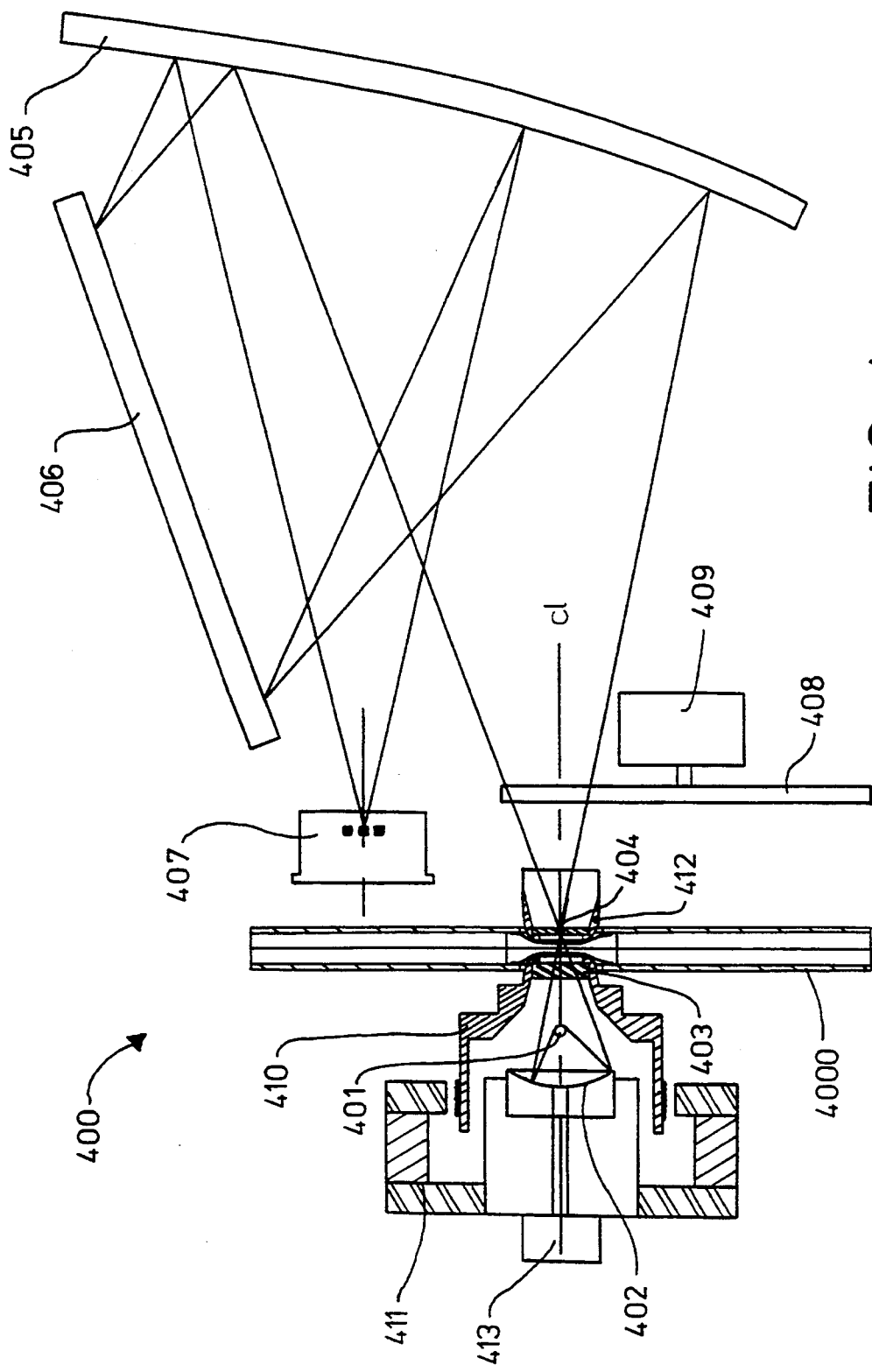
FIG. 4 shows a partial cross section of an optical unit in an analyzer according to the invention and a measuring chamber device according to the invention for photometric determination of an analyte in a sample with a schematic representation of the components of the optical unit.

FIG. 4 shows a prototype of an optical unit 400 for use in the determination of an analyte in a sample. The sample is located in the measuring chamber device 4000, which is secured between a movable part 410 and a stationary part 412. The movable part 410 may be displaced along the centre line cl by means of an electromagnet 411. The optical unit 400 comprises a radiation source 401 in the form of a thermal radiation unit, more specifically a CrNi filament heated to a temperature of approx. 1050° C. The radiation source 401 is specially made for the present purpose by Applicant. The optical unit 400 further comprises a reference diode 413 of the type SFH 225 from Siemens, Munich, Germany, which regulates the radiation of the filament 401.

Figure 5A:
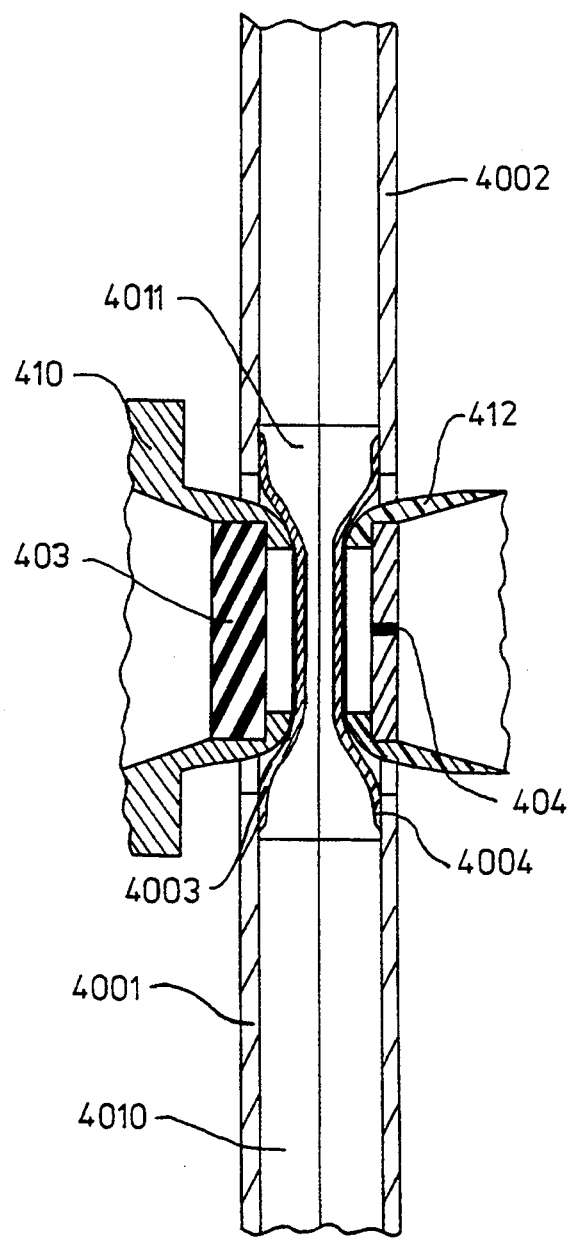
FIGS. 5a and b show partial cross sections of a measuring chamber device according to the invention and of the parts of an optical unit in an analyzer according to the invention between which the measuring chamber device is secured when measuring, the measuring chamber device and the securing parts being shown in two different positions in relation to each other.

Radiation from the radiation source 401 is transmitted to a parabolic mirror 402 ($\phi$ 10 mm, f=3 mm) specially made for the present purpose by Applicant. The parabolic mirror 402 transmits the radiation from the filament 401 through a band-pass filter 403 (center value 4240 nm, half band width 200 nm) from Spektrogon, Täby, Sweden, and from there through the blood sample in the measuring chamber device 4000. From the measuring chamber device 4000, the radiation is transmitted through a slit 404 (0.5×3 mm) located on a sapphire window ($\phi$3×0.4 mm), past a chopper 408, which by means of a DC motor 409 provides a chopper frequency of approx. 800 Hz. After passage of the chopper 408, the radiation falls onto an off-axis parabolic mirror 405 (f=65 mm) specially made by Applicant which reflects the radiation as a parallel pencil onto a grating 406 (a 300-lines grating optimized to approx. 4.3 μm) from Optometrics, Leeds, England. The grating 406 deflects the radiation back onto the parabolic mirror 405, which focuses the radiation onto a detector 407 from Hamamatsu, Hamamatsu City, Japan. The detector 407 comprises a diode array consisting of three PbSe-diodes (0.5×2 mm, center distance 1 mm) built-into a T05-housing with a band-pass filter (center value 4400 nm, half band width 650 nm). The diodes in the diode array 407 register the intensity of radiation at their respective of the three measuring wavelengths, which are separated by means of the grating 406 and the off-axis parabolic mirror 405. From the diodes electric signals representing the intensity of radiation incoming to the diodes are sent to a analog/digital converter (not shown) and from there to a data processing unit (not shown) performing the calculations of the content of $CO_2$ in the sample on the basis of the signals received. FIGS. 5a and b show a partial section corresponding to FIG. 1c through a measuring chamber device 4000 according to the invention placed between the movable part 410 and the stationary part 412 of an optical unit for measuring of the $CO_2$ content in a sample. As described in connection with FIG. 4 measuring radiation is transmitted through a band-pass filter 403 in the movable part 410, through the measuring chamber device 4000 to the slit 404 in the stationary part 412.

When a measuring chamber device 4000 is arranged in the analyzer, the movable part 410 of the optical unit is displaced towards one of the windows 4003 of the measuring chamber device and pushes the measuring chamber device 4000 and the opposite window 4004 towards the stationary part 412 of the optical unit. The measuring chamber device 4000 is now secured in the optical unit with one window 4003 adjacent to the movable part 410 and the second window 4004 adjacent to the stationary part 412. By displacing the movable part 410 into several predetermined positions, the windows 4003 and 4004 are displaced transversely to the measuring chamber 4011 and the measuring conduit 4010 thereby varying the distance between the windows in a predetermined manner. This adjustment in shape of the measuring chamber 4011 results in setting the radiation path length across the measuring chamber.

Figure 5B:
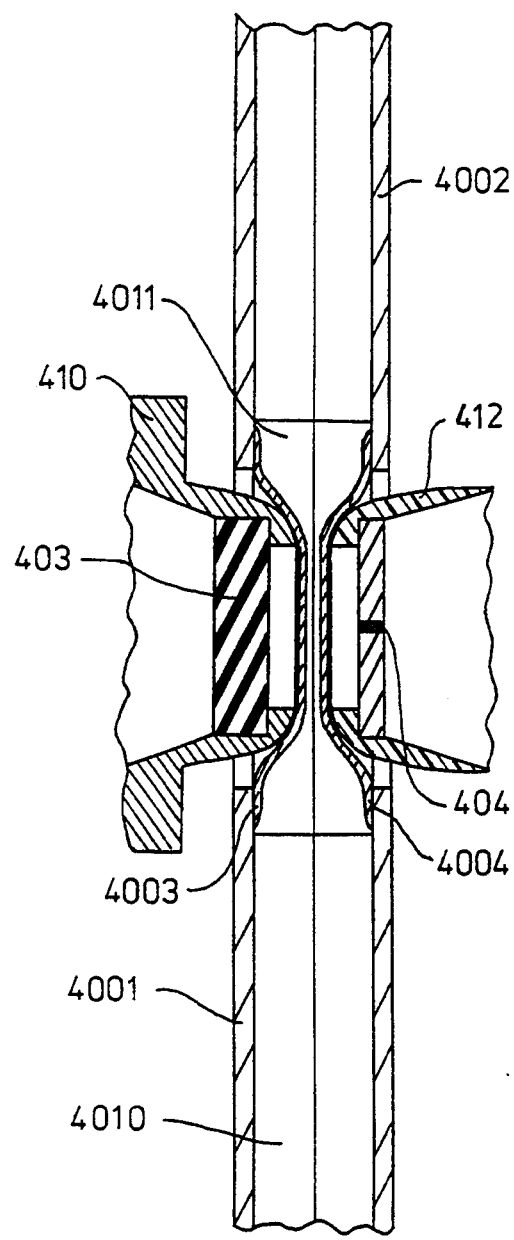

In the position shown in FIG. 5a the movable part 410 of the optical unit is displaced to a first position, and the distance between the windows 4003 and 4004 of the measuring chamber device 4000 defines a first radiation path length across the measuring chamber corresponding to for example 100 $\mu$m. In FIG. 5b the movable part 410 is displaced to a second position, and a second radiation path length corresponding to for example 50 $\mu$m is defined. By giving the movable part 410 and the stationary part 412 of the optical unit the same external shape in the areas getting in contact with the windows 4003 and 4004, a uniform, symmetric displacement of the windows 4003 and 4004 and thus of the measuring chamber 4011 is ensured.

As mentioned in connection with FIGS. 1a-c the foil for the windows 4003 and 4004 is stretched during mounting in the halves 4001 and 4002 of the measuring chamber device to ensure plane windows after ultrasonic welding. When displacing the windows 4003 and 4004 between the two measuring positions, the thickness of the windows will change. However, this change may be so minimal that its influence on the determination of the analyte may be disregarded. This is clarified by the following example:

When a foil window corresponding to the windows 4003 and 4004 is displaced 100 $\mu$m from the resting position and from this position is displaced an additional 25 $\mu$m, the tension in the window causes an insignificant change of thickness, viz. approx. 12 nm, which is considerably less than the thickness variations between the windows in mass-produced measuring chamber devices. The thickness change of the window due to the displacement results in a negligible change in the period of the above described sinusoidal interference spectrum of approx. 0.1 nm. Due to the fact that the thickness change of the windows 4003 and 4004 is negligible during the displacement the interference caused by the windows 4003 and 4004 in the measuring situations shown in FIGS. 5a and b may be regarded similar.

Figure 6:
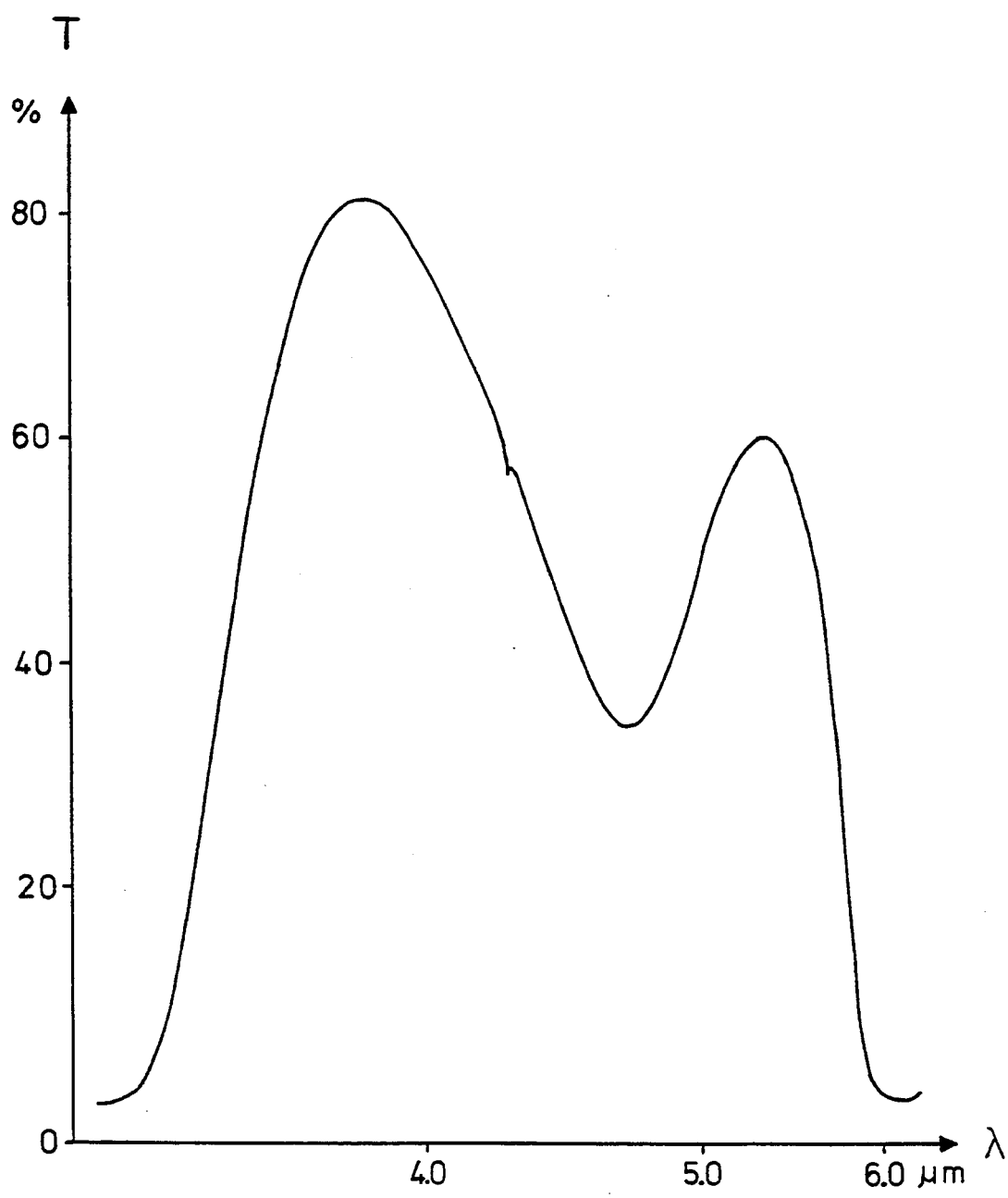
FIG. 6 shows an absorption spectrum for water having a $CO_2$ content of approx. 100 mmHg.

FIG. 6 shows an absorption spectrum in the wavelength range 3300–6000 nm for water with a content of $CO_2$ of approx. 100 mmHg and a radiation path length of approx. 100 $\mu$m. The spectrum is recorded at an IR spectrophotometer of the type Beckman IR9. It appears from the figure that a content of $CO_2$ causes absorption at a wavelength of approx. 4268 nm. However, said absorption is, as seen, small in relation to the absorption caused by the water. Due to the fact that absorption on account of $CO_2$ is relatively small in relation to absorption caused by water interferences caused by, for example the measuring chamber device, the optical system, the surroundings, etc., may have a substantial effect on the measurement result. As seen from FIG. 6, a $CO_2$ content of approx. 100 mmHg and a radiation path length of approx. 100 $\mu$m will cause a change of the transmission of around 3% only. When comparing this with the foil spectrum in FIG. 3, from which it appears that the sinusoidal superposition deriving from interference in the surfaces of the foil causes a variation in the transmission spectrum of around 5%, it appears that the interference spectrum from the foil windows will strongly influence the actual measuring spectrum. Thus, it is necessary to either remove the unwanted interferences or compensate therefor in the calculation of the $CO_2$ content in the sample.

Figure 7:
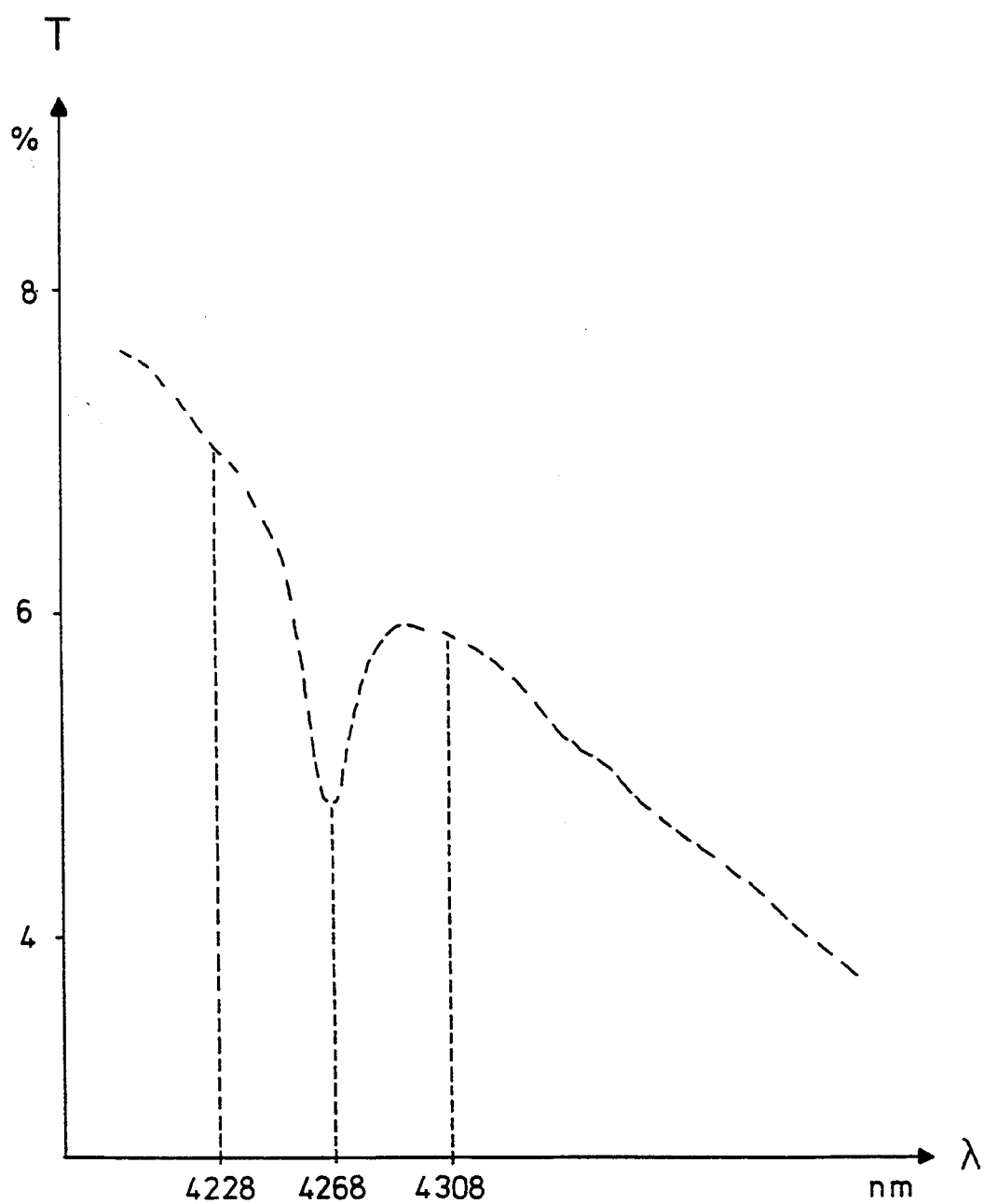
FIG. 7 shows an absorption spectrum for whole blood adjusted to a $CO_2$ content of approx. 419 mmHg by tonometry.

FIG. 7 shows an absorption spectrum for whole blood adjusted to a $CO_2$ content of approx. 419 mmHg by tonometry. The spectrum is like the previous one recorded on an IR spectrophotometer of the type Beckman IR9. It appears from this absorption spectrum as well that a content of $CO_2$ in the sample causes absorption at a wavelength of approx. 4268 nm.

Figure 8:
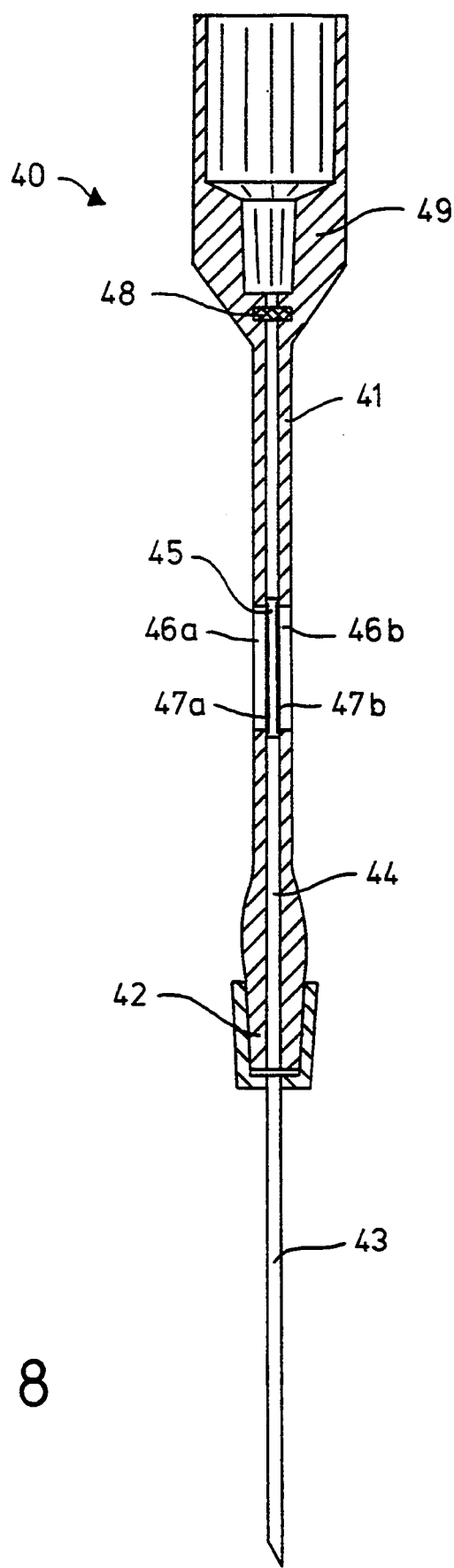
FIG. 8 shows a view of a preferred embodiment of a measuring chamber device according to the invention for use in determination of the $CO_2$ content in a sample of whole blood.

FIG. 8 shows a preferred embodiment of a measuring chamber device 40 according to the invention for determination of the $CO_2$ content in a sample of whole blood. The measuring chamber device 40 is provided as a sampling device in which the blood sample is transferred directly from a patient to the measuring chamber device.

The measuring chamber device 40 comprises a body 41 consisting of two parts which after assembly form an internal continuous sample conduit 44 with a cross section of 0.3×2 mm. At the end of the body 41, where the inlet of the conduit is located, the body 41 is provided with a Luer cone 42 and thus adapted to be connected to a needle 43 of the type usually employed for blood sampling. At the end opposite the inlet opening, the conduit 44 is provided with a hydrophilic/hydrophobic filter 48, and at this end 49 the body 41 is adapted for coupling to a traditional plunger syringe which may serve as an sampling aid in special situations.

Around the middle of the conduit 44 it expands while forming a measuring chamber 45 with a diameter of 8.6 mm. At this location each of the two parts of the body 41 comprise a through hole 46a, 46b perpendicular to the conduit 44 and having a diameter of 6.0 mm, said holes facing each other after assembly of the body 41. On the inside of the conduit 44 each of the holes 46a, 46b are covered by a foil window 47a and 47b, respectively, of a diameter corresponding to the measuring chamber 45 and made from a 23 $\mu$m polyethylene terephthalate foil. Prior to assembly of the body 41 the foil windows 47a, 47b are mounted by means of ultrasonic welding in a manner as described above in connection with FIGS. 1a–c. Thus, the measuring chamber 45 is delimited transversely to the conduit 44 by the two windows 47a, 47b.

The theoretical background of the method according to the invention is described in the following wherein the analyte is exemplified by $CO_2$.

When transmitting radiation with wavelength $\lambda$ and intensity $I_\lambda$ in an optical system and through a measuring chamber having a radiation path length l and measuring the intensity $I_{l,\lambda}$ of the transmitted radiation, the total absorbance $A_{l,\lambda}$ of the optical system and the sample may be determined as:

$$A_{l,\lambda} = \log(I_\lambda/I_{l,\lambda}) \qquad (2)$$

Said absorbance consists of the sum of the absorbances of the various components and may be written as:

$$A_{l,\lambda} = A_{l,\lambda}(H_2O) + A_{l,\lambda}(CO_2) + A_{l,\lambda}(i_b) + A_\lambda(i_f) + A_\lambda(i_a) + A_\lambda(i_o) \qquad (3)$$

where $\lambda$ is the wavelength of the transmitted radiation;
l is the radiation path length across the measuring chamber;
$A_{l,\lambda}(H_2O)$ is the absorption caused by water in the sample;
$A_{l,\lambda}(CO_2)$ is the absorption caused by $CO_2$ in the sample;
$A_{l,\lambda}(i_b)$ is the absorption caused by other analytes in the sample;
$A_{l,\lambda}(i_f)$ is the absorption caused by the windows of the measuring chamber;
$A_{l,\lambda}(i_a)$ is the absorption caused by the atmosphere; and
$A_{l,\lambda}(i_o)$ is the absorption caused by the optical system.

The first three terms of (3) depend on the composition of the sample and on the radiation path length across the measuring chamber, whereas the last three terms depend on the measuring chamber device, the optical system, and the atmosphere, but are independent of the sample.

When performing two measurement steps at their respective radiation path lengths l1, l2 across the measuring chamber (cf. FIGS. 5a and b) and using radiation having the radiation intensities $I_{\lambda,1}$ and $I_{\lambda,2}$, respectively, the total absorbance $A_{l1,\lambda}$ and $A_{l2,\lambda}$, c.f. (3), for each step is obtained. By taking the difference $\Delta A_\lambda = A_{l1,\lambda} - A_{l2,\lambda}$ between said absorbances, the last three terms of (3) are left out:

$$\begin{aligned}\Delta A_\lambda = A_{l1,\lambda} - A_{l2,\pi} &= \log(I_{\lambda,1}/I_{l1,\lambda}) - \log(I_{\lambda,2}/I_{l2,\lambda}) \\ &= \log(I_{\lambda,1}/I_{\lambda,2}) + \log(I_{l2,\lambda}/I_{l1,\lambda}) \\ &= A_{l1,\lambda}(H_2O) - A_{l2,\lambda}(H_2O) + \\ &\quad A_{l1,\lambda}(CO_2) - A_{l2,\lambda}(CO_2) + \\ &\quad A_{l1,\lambda}(i_b) - A_{l2,\lambda}(i_b)\end{aligned} \qquad (4)$$

When the intensities $I_{\lambda,1}$ and $I_{\lambda,2}$ of the incoming radiation at the two radiation path lengths l1 and l2 are the same, the calculations are made independent of the intensity as the term $\log(I_{\lambda,1}/I_{\lambda,2})$ equals zero. Thus, in the calculations it is only necessary to know the intensities of the transmitted radiation $I_{l1,\lambda}$ and $I_{l2,\lambda}$. According to Lambert-Beer's Law the absorbance $A_\lambda$ relating to a given analyte at a given wavelength $\lambda$ is determined as:

$$A_\lambda(CO_2) = \epsilon_\lambda(CO_2) \cdot l \cdot C(CO_2) \qquad (5)$$

where $\epsilon_\lambda(CO_2)$ is the molecular absorption coefficient for $CO_2$ at the wavelength $\lambda$;
l is the radiation path length through the sample containing $CO_2$; and
$C(CO_2)$ is the molecular concentration of $CO_2$ in the sample.

By introducing Lambert-Beer's Law (5) in the expression for $\Delta A_\lambda$, cf. (4) the following expression is obtained:

$$\begin{aligned}\Delta A_\lambda &= \log(I_{l2,\lambda}/I_{l1,\lambda}) \\ &= \epsilon_\lambda(H_2O) \cdot (l1 - l2) \cdot C(H_2O) + \epsilon_{80}(CO_2) \cdot (l1 - l2) \cdot C(CO_2) + \epsilon_\lambda(i_b) \cdot (l1 - l2) \cdot C(i_b) \\ &= \epsilon_\lambda(H_2O) \cdot \Delta l \cdot C(H_2O) + \epsilon_\lambda(CO_2) \cdot \Delta l \cdot C(CO_2) + \epsilon_\lambda(i_b) \cdot \Delta l \cdot C(i_b)\end{aligned} \qquad (6)$$

where $\Delta l = l1 - l2$ may be considered as the effective radiation path length through the sample.

The last term of (6) corresponds to absorption deriving from other analytes in the sample. It has proved allowable to consider said term as deriving from only one analyte, $i_b$, the molar concentration $C(i_b)$ of which then becomes a theoretical value.

When measuring on blood, it is usually desired that the content of $CO_2$ is expressed by its partial pressure.

The relationship between the concentration of $CO_2$ in a fluid sample and the partial pressure of $CO_2$ in the sample may be written as:

$$C(CO_2) = \alpha_t(CO_2) \cdot pCO_2 \qquad (7)$$

where $\alpha_t(CO_2)$ is the solubility coefficient for $CO_2$ in the sample at the temperature t; and
$pCO_2$ is the partial pressure of $CO_2$ in the sample.

When introducing (7) into the second term of (6) the following expression is obtained:

$$\begin{aligned}\Delta A_\lambda &= \epsilon_\lambda(H_2O) \cdot \Delta l \cdot C(H_2O) + \epsilon_\lambda(CO_2) \cdot \alpha_t(CO_2) \cdot \Delta l \cdot pCO_2 + \epsilon_\lambda(i_b) \cdot \Delta l \cdot C(i_b) \\ &= \epsilon_\lambda'(H_2O) \cdot \Delta l + \epsilon_\lambda'(CO_2) \cdot \Delta l \cdot pCO_2 + \epsilon_\lambda(i_b) \cdot \Delta l \cdot C(i_b) \\ &= \epsilon_\lambda'(H_2O) \cdot \Delta l + \epsilon_\lambda'(CO_2) \cdot C'(CO_2) + \epsilon_\lambda(i_b) \cdot C'(i_b)\end{aligned} \qquad (8)$$

where
$\epsilon_\lambda'(H_2O) = \epsilon_\lambda(H_2O) \cdot C(H_2O)$;
$\epsilon_\lambda'(CO_2) = \epsilon_\lambda(CO_2) \cdot \alpha_t(CO_2)$;
$C'(CO_2) = \Delta l \cdot pCO_2$; and
$C'(i_b) = \Delta l \cdot C(i_b)$ When for each radiation path length l1, l2 measurements are made at three wavelengths $\lambda 1$, $\lambda 2$, $\lambda 3$, the following three equations, cf. (8), may be set up:

$$\Delta A_{\lambda 1} = \epsilon_{\lambda 1}'(H_2O) \cdot \Delta l + \epsilon_{\lambda 1}'(CO_2) \cdot C'(CO_2) + \epsilon_{\lambda 1}(i_b) \cdot C'(i_b)$$

$$\Delta A_{\lambda 2} = \epsilon_{\lambda 2}'(H_2O) \cdot \Delta l + \epsilon_{\lambda 2}'(CO_2) \cdot C'(CO_2) + \epsilon_{\lambda 2}(i_b) \cdot C'(i_b)$$

$$\Delta A_{\lambda 3} = \epsilon_{\lambda 3}'(H_2O) \cdot \Delta l + \epsilon_{\lambda 3}'(CO_2) \cdot C'(CO_2) + \epsilon_{\lambda 3}(i_b) \cdot C'(i_b) \qquad (9)$$

From said three equations the three unknown quantities $\Delta l$, $C'(CO_2)$ and $C'(i_b)$ may be calculated, and the partial pressure of $CO_2$ in the sample may be determined as:

$$pCO_2 = C'(CO_2)/\Delta l \qquad (10)$$

When the method according to the invention is to be performed in practice the absorption coefficient matrix $$E = \begin{pmatrix} \epsilon_{\lambda 1}'(H_2O) & \epsilon_{\lambda 1}'(CO_2) & \epsilon_{\lambda 1}(i_b) \\ \epsilon_{\lambda 2}'(H_2O) & \epsilon_{\lambda 2}'(CO_2) & \epsilon_{\lambda 2}(i_b) \\ \epsilon_{\lambda 3}'(H_2O) & \epsilon_{\lambda 3}'(CO_2) & \epsilon_{\lambda 3}(i_b) \end{pmatrix} \quad (11)$$

is predetermined experimentally by measuring for each of the wavelengths λ1, λ2, λ3 samples of particular known compositions. Determination of the absorption coefficient matrix E is illustrated in the following example.

A sample-containing measuring chamber device corresponding to the one shown in FIG. 8 is inserted into an optical system wherein the radiation path length may be set accurately and thus is known. Radiation is transmitted from the radiation source through the measuring chamber to the radiation detector. Measurements are performed at the three wavelengths λ1=4228 nm, λ2=4268 nm, λ3 =4308 nm with a band width of approx. 20 nm and at the radiation path lengths l1=100 μm and l2 =50 μm. The intensity of the transmitted radiation at the three wavelengths is kept constant.

For each wavelength λ1-λ3 measurements are performed on a sample of pure water without $CO_2$ or other analytes. On the basis of the measured absorption for each wavelength, the absorption coefficients relating to water are determined by means of Lambert-Beer's Law, cf. (5). As absorption deriving from $CO_2$ at the wavelengths λ1=4228 nm and λ3=4308 nm is insignificant compared to $CO_2$ absorption at the wavelength λ2=4268 nm, the absorption coefficients $\epsilon_{\lambda 1}'(CO_2)$ and $\epsilon_{\lambda 3}'(CO_2)$ are set to 0.0. The absorption coefficient $\epsilon_{\lambda 2}'(CO_2)$ is determined by measuring a sample of water with a known content of $CO_2$ without other analytes. On the basis of the previously determined absorption coefficients for water, the radiation path length across the measuring chamber and the $CO_2$ content in the sample, $\epsilon_{\lambda 2}'(CO_2)$ may be determined.

In the determination of the $CO_2$ content in a sample it is essential to consider the absorption caused by other analytes in the sample $(\epsilon\lambda(i_b) \cdot C'(i_b))$ - the particular values for $\epsilon(i_b)$ and $C'(i_b)$ are unimportant. As mentioned previously, $C'(i_b)$ is only a theoretical value of no real physical importance. Therefore, the determination of the absorption coefficients $\epsilon_{\lambda 1}(i_b)$, $\epsilon_{\lambda 2}(i_b)$, $\epsilon_{\lambda 3}(i_b)$ is not a matter of determining these coefficients definitely, but determining the ratios among them.

The absorption coefficients $\epsilon_{\lambda 1}(i_b)$, $\epsilon_{\lambda 2}(i_b)$ and $\epsilon_{\lambda 3}(i_b)$ are determined by measuring at the three measuring wavelengths λ1, λ2, λ3 on a sample of whole blood with a known content of water and $CO_2$. An equation set corresponding to (9) may be set up. The terms deriving from water and $CO_2$ may be calculated on the basis of the previously derived absorption coefficients and deducted from the equations. Three equations are left expressing the relation between absorption caused by other analytes at each of the three wavelengths. The relation between these absorbances corresponds to the relation among the absorption coefficients $\epsilon_{\lambda 1}(i_b)$, $\epsilon_{\lambda 2}(i_b)$ and $\epsilon_{\lambda 3}(i_b)$, as $C'(i_b)$ is the same at the three wavelengths.

The smallest of the absorption coefficients is set to $1.0 \cdot 10^{-3}$ μm being of the same magnitude as the absorption coefficients for water, and the other coefficients are determined relatively thereto.

The absorption coefficient matrix is determined as:

$$E = \begin{pmatrix} \epsilon_{4228}'(H_2O) & \epsilon_{4228}'(CO_2) & \epsilon_{4228}(i_b) \\ \epsilon_{4268}'(H_2O) & \epsilon_{4268}'(CO_2) & \epsilon_{4268}(i_b) \\ \epsilon_{4308}'(H_2O) & \epsilon_{4308}'(CO_2) & \epsilon_{4308}(i_b) \end{pmatrix} \quad (12)$$

$$= \begin{pmatrix} 10.50 \cdot 10^{-3} \mu m^{-1} & 0.0 & 1.59 \cdot 10^{-3} \mu m^{-1} \\ 11.12 \cdot 10^{-3} \mu m^{-1} & 2.8 \cdot 10^{-6} mmHg^{-1} \mu m^{-1} & 1.37 \cdot 10^{-3} \mu m^{-1} \\ 11.75 \cdot 10^{-3} \mu m^{-1} & 0.0 & 1.00 \cdot 10^{-3} \mu m^{-1} \end{pmatrix}$$

When measuring on a sample of whole blood it is required, as mentioned previously, to measure at short radiation path lengths through the sample as the water content in the sample causes relatively large absorption. Relevant radiation path lengths for measuring on whole blood fall in a range from about zero to max. 200 μm. However, the radiation path length must not so short that standing waves are produced between the inside of the measuring chamber walls, or in practice no less than approx. 25 μm.

In order to improve the measurement results it is preferred to perform the measurement steps three times. A measurement thus comprises setting the radiation path length initially to approx. 100 μm, then to 50 μm, again to 100 μm, then to 50 μm and again to 100 μm and then 50 μm. At each radiation path length the intensity of the radiation transmitted through the measuring chamber is measured during 5 seconds. On the basis of the "three sets" of absorptions obtained three values for $pCO_2$ are determined, and the content of $CO_2$ in the sample is calculated as the mean value.

The advantage of the method according to the invention, by which measurements are performed at different radiation path lengths compared to a prior art method by which the radiation path length is kept constant, is clearly seen from the following comparative example.

Determination of the $CO_2$ content in gas samples was performed in two experiments. In the method used for the first experiment the radiation path length was kept constant at 65 μm during the entire course of measuring. In the method used for the second experiment the radiation path length was varied between 50 μm and 100 μm as described above.

In each experiment measurements were performed on a set of gases consisting of 3 gases each having a different composition of $CO_2$, $O_2$ and $N_2$. Two not quite identical sets of gases were used, the lack of identity being of no importance in the present context. In Table 1 the compositions of the gases are listed. Index A denotes a gas used for the first experiment and index B denotes a gas used for the second experiment.

TABLE 1

| GAS | The composition of measuring gases. | | |
|---|---|---|---|
| | % $CO_2$ | % $O_2$ | % $N_2$ |
| 1A | 13.040 | 2.036 | 84.924 |
| 1B | 13.520 | 2.000 | 84.480 |
| 2A | 5.631 | 11.270 | 83.099 |
| 2B | 5.708 | 11.309 | 82.983 |
| 3A | 1.408 | 18.150 | 80.442 |
| 3B | 1.404 | 18.170 | 80.426 |

In each set of gases one gas (GAS 2A or 2B) has a content of $CO_2$ and $O_2$ normal for blood. The remaining gases have a composition different from this. One has a larger content of $CO_2$ and a smaller content of $O_2$ (GAS 1A and 1B) and the other has a larger content of $O_2$ and a smaller content of $CO_2$ (GAS 3A and 3B).

For each of the gases GAS 1A, 1B, 3A and 3B the content of $CO_2$ in the gas was determined on the basis of five subsequent measurements in the same measuring chamber. The mean value of the five $CO_2$ determinations and the standard deviations were calculated.

In each of the gases GAS 2A and 2B the content of $CO_2$ in the gas was determined three times by use of three different measuring chambers. Five measurements are performed with each of the three measuring chambers, and the mean values and standard deviations are calculated, as described for the gases 1A-3B above.

The results from the measurements performed appear in Tables 2 and 3 below, where Table 2 lists the results from the first experiment, and Table 3 lists the results from the second experiment.

In the tables
x is the mean value from five measurements of $pCO_2$ in the same measuring chamber; and
s is the standard deviation.

TABLE 2

| $pCO_2$ | Measuring results from the prior art method. | | | | |
|---|---|---|---|---|---|
| | GAS 1A | GAS 2A | | | GAS 3A |
| x mmHg | 126.38 | 81.46 | 91.01 | 27.00 | −22.86 |
| s mmHg | 3.20 | 2.47 | 7.75 | 24.32 | 20.18 |

TABLE 3

| $pCO_2$ | Measuring results from the method according to the invention. | | | | |
|---|---|---|---|---|---|
| | GAS 1B | GAS 2B | | | GAS 3B |
| x mmHg | 109.40 | 42.84 | 41.62 | 42.40 | 5.30 |
| s mmHg | 1.47 | 1.05 | 1.04 | 1.07 | 0.95 |

When comparing the results from the two experiments (Table 2 and 3) it is clearly seen that measuring according to the invention at two radiation path lengths across the measuring chamber is highly advantageous.

As appearing from Table 2 the results for GAS 2A are totally unacceptable. The mean values differ very much and the standard deviations obtained for measurements performed in the same measuring chamber are extensive.

In the second experiment when measuring on GAS 2B the mean values obtained from the different measuring chambers do not vary much and the standard deviation is reduced considerably.

When studying the results from measuring the other gases (GAS 1A, 1B, 3A and 3B), it is also apparent that the method according to the invention is superior to the prior art method.

The above-mentioned use of the method may, of course, be used for determination of other analytes than $CO_2$, and it is no condition that the solvent is water. For other analytes and/or solvents it is in each particular case required to determine the absorption coefficient matrix, cf. (11).

When the analyzer, by means of which a sample is to be analyzed, is designed in such a manner that the radiation path length across the measuring chamber may be set accurately, the above-mentioned determination of a given analyte in a sample may be performed by measuring at two wavelengths only. Hereby the equation set on the basis of which the analyte content is determined will include only two equations with two unknown quantities.

In the example shown above the solvent (water) is strongly absorbing at the selected measuring wavelengths. In case it is desired to determine the content of an analyte in a sample, in which the solvent does not absorb at the measuring wavelengths, the equation set, cf. (9), for the calculations will also include only two equations. Further, when using an analyzer wherein the radiation path length may be set accurately, the equation set will be further reduced. In this case it will be required to measure at one wavelength only and thus the analyte content may be determined from one equation with one unknown quantity.

Similarly, the content of more analytes in a sample may be determined by measuring in the same measuring chamber. In equation (3) the absorbance contribution for the analyte/analytes is incorporated, and measuring is performed at one/several further wavelengths. Accordingly, an equation set corresponding to (9) may be set up; this equation set contains one or several further equations and unknown quantities depending on how many further analytes are to be determined.

To ensure a uniform adjustment of the measuring chamber in a measuring chamber device according to the invention, it is preferred that the measuring chamber be symmetrically designed, cf. FIGS. 1a-c and FIG. 8. Moreover, in that case the measuring chamber device need not be oriented in a particular way in relation to the related optical system.

The measuring chamber may, if desired, be designed asymmetrically, for example the partially transparent areas may be different in thickness, area size and/or be made from different materials. Further, only one side of the measuring chamber need be adjustable. With this asymmetrical design it is required that the measuring chamber device be oriented in a particular way in relation to the optical system made especially for this measuring chamber device.

Furthermore, the measuring chamber may comprise a partially transparent wall part on one side of the chamber and an opposite wall part reflecting the radiation. In the corresponding optical system the radiation transmission paths for radiation transmitted towards the measuring chamber device and for radiation transmitted from the measuring chamber, respectively, lie on the same side of the measuring chamber device.

The measuring chamber device may be made in several other embodiments provided that the measuring chamber is adapted to interact with a corresponding optical system and that the adjustment in shape of the measuring chamber controls the setting of the radiation path length across the measuring chamber.

I claim:

1. A method of photometric in vitro determination of the content of an analyte in a sample, the method comprising:
   A) providing a measuring chamber for holding the sample, the measuring chamber comprising at least one partially transparent wall in optical communication with the sample, wherein the measuring chamber receives radiation through the at least one partially transparent wall and transmits the radiation over a path having a path length through the sample and out of the chamber through the at least one partially transparent wall, a shape of the measuring chamber being adjustable for varying the path length through the chamber;
   B) providing an optical system comprising a radiation source and a radiation detector;
   C) mounting the measuring chamber in optical communication with the radiation source for transmitting radiation into the sample through the at least one partially transparent wall, and mounting the measuring chamber in optical communication with the radiation detector for receiving the radiation transmitted through the sample;
   D) setting in a first measuring step a first unknown radiation path length through the measuring chamber, and transmitting radiation at at least two wavelengths from the radiation source through the measuring chamber and to the radiation detector;
   E) in a second measuring step, adjusting the shape of the measuring chamber and thereby setting a second unknown radiation path length across the measuring chamber, and transmitting radiation at the same at least two wavelengths as used during the first measuring step from the radiation source through the measuring chamber and to the radiation detector; and
   F) determining the analyte content of the sample from the absorbance of the sample detected in each of the measuring steps, the determination being independent of the change in path length, the determination being made by solving simultaneous equations.

2. The method according to claim 1 wherein the measuring chamber has optical transmission properties, the optical transmission properties being essentially independent of the shape adjustment of the measuring chamber.

3. The method according to claim 1 wherein the measuring chamber comprises two at least partially transparent opposite walls along the radiation path, the radiation being received through one wall, and transmitted out of the other wall.

4. The method according to claim 3 wherein the adjustment in shape of the measuring chamber comprises displacement of one of the two opposite at least partially transparent walls.

5. The method according to claim 3 wherein the adjustment in shape of the measuring chamber comprises displacement of each of the two opposite at least partially transparent walls.

6. The method according to claim 1 wherein the measuring chamber comprises a wall opposite the at least one partially transparent wall, the opposite wall reflecting incoming radiation back through the at least one partially transparent wall.

7. The method according to claim 6 wherein the adjustment in shape of the measuring chamber comprises displacement of the at least one partially transparent wall.

8. The method according to claim 6 wherein the adjustment in shape of the measuring chamber comprises displacement of the opposite wall.

9. The method according to claim 6 wherein the adjustment in shape of the measuring chamber comprises displacement of each of the opposite wall and the at least one partially transparent wall.

10. The method according to claim 1 wherein the transmitted radiation is wide-band radiation, and wherein one of the at least two wavelengths is a wavelength at which the analyte absorbs.

11. The method according to claim 1 wherein the analyte is $CO_2$.

12. The method according to claim 11 further comprising transmitting and detecting radiation at three wavelengths during each of the measuring steps, wherein the wavelengths are approximately 4228 nm, 4268 nm and 4308 nm, each having a band width of approx. 20 nm.

13. The method according to claim 1 further comprising transmitting and detecting radiation at more than two wavelengths during each of the measuring steps.

14. An analyzer for performing photometric in vitro determination of the content of an analyte in a sample, the analyzer comprising:
   A) a measuring chamber for holding the sample, the measuring chamber comprising at least one partially transparent wall in optical communication with the sample, wherein the measuring chamber receives radiation through the at least one partially transparent wall and transmits the radiation over a path having a path length through the sample and out of the chamber through the at least one partially transparent wall, a shape of the measuring chamber being adjustable for varying the path length through the chamber;
   B) an optical system comprising
      i) a radiation source for generating at least two wavelengths of radiation, the at least one partially transparent wall of the measuring chamber being mounted in optical communication with the radiation source for receiving radiation at the at least two wavelengths from the source into the sample; and
      ii) a radiation detector for detecting the at least two wavelengths of radiation, the at least one partially transparent wall of the measuring chamber being mounted in optical communication with the radiation detector for transmitting the radiation of the at least two wavelengths through the sample and to the detector;
   C) means for setting in a first measuring step a first unknown radiation path length through the measuring chamber, the radiation source transmitting radiation at the at least two wavelengths through the measuring chamber, the radiation detector detecting the radiation at the at least two wavelengths;
   D) means for adjusting the shape of the measuring chamber and thereby setting a second unknown radiation path length across the measuring chamber in a second measuring step, the radiation source transmitting radiation at the same at least two wavelengths as during the first measuring step across the measuring chamber, the radiation detector detecting the radiation at the same at least two wavelengths; and E) means for determining the analyte content of the sample from the absorbance of the sample detected in each of the measuring steps by solving simultaneous equations, the determination being independent of the change in path length.

15. The analyzer according to claim 14, wherein the means for adjusting the shape of the measuring chamber comprises:

the radiation source or radiation detector being movable and being movable, the interacting with the movable wall to adjust the shape of the chamber.

16. The analyzer according to claim 14, wherein the measuring chamber has optical transmission properties, the optical transmission properties being essentially independent of the shape of the measuring chamber.

17. The analyzer according to claim 14, wherein the measuring chamber comprises two at least partially transparent opposite walls along the radiation path, the radiation being received through one wall, and transmitted out of the other wall.

18. The analyzer according to claim 17, wherein one of the two opposite at least partially transparent walls is movable, and the means for adjusting the shape of the measuring chamber comprises means for displacing the movable of the two at least partially transparent walls.

19. The analyzer according to claim 17, wherein each of the two opposite at least partially transparent walls is movable, and the means for adjusting the shape of the measuring chamber comprises means for displacing each of the movable opposite at least partially transparent walls.

20. The analyzer according to claim 14, wherein the measuring chamber comprises a wall opposite the at least one partially transparent wall, the opposite wall reflecting incoming radiation back through the at least one partially transparent wall.

21. The analyzer according to claim 20, wherein the at least one partially transparent wall is movable, and the means for adjusting the shape of the measuring chamber comprises means for displacing the at least one partially transparent wall.

22. The analyzer according to claim 20, wherein the opposite wall is movable, and the means for adjusting the shape of the measuring chamber comprises means for displacing the opposite wall.

23. The analyzer according to claim 20, wherein each of the opposite wall and the at least one partially transparent wall is movable, and the means for adjusting the shape of the measuring chamber comprises means for displacing each of the opposite wall and the at least one partially transparent wall.

24. The analyzer according to claim 14, wherein the transmitted radiation is wide-band radiation, and wherein one of the at least two wavelengths is a wavelength at which the analyte absorbs.

25. The analyzer according to claim 14, wherein the analyte is $CO_2$.

26. The analyzer according to claim 25, wherein the radiation source is adapted for transmitting radiation at three wavelengths through the measuring chamber during each of the measuring steps, and the radiation detector is adapted for detecting the radiation at the same three wavelengths during each of the measuring steps, and wherein the three wavelengths are approximately 4228 nm, 4268 nm and 4308 nm, each having a band width of approx. 20 nm.

27. The analyzer according to claim 14, wherein the radiation source is adapted for transmitting radiation at more than two wavelengths through the measuring chamber during each of the measuring steps, and the radiation detector is adapted for detecting the radiation at each of the more than two wavelengths during each of the measuring steps.

* * * * *

UNITED STATES PATENT AND TRADEMARK OFFICE
CERTIFICATE OF CORRECTION

PATENT NO. : 5,371,020

DATED : December 6, 1994

INVENTOR(S): Peter Aage Frischauf

It is certified that error appears in the above-identified patent and that said Letters Patent is hereby corrected as shown below:

Claim 15, line 12: Insert -- a wall of the measuring chamber adjacent to the movable radiation source or radiation detector -- before "being movable";

Claim 15, line 12: Insert -- movable radiation source or radiation detector -- before "interacting".

Signed and Sealed this

Thirtieth Day of May, 1995

Attest:

Attesting Officer

BRUCE LEHMAN

Commissioner of Patents and Trademarks